(12) United States Patent
Gilleland et al.

(10) Patent No.: US 6,649,188 B2
(45) Date of Patent: *Nov. 18, 2003

(54) HIGHLY FLEXIBLE STARCH-BASED FILMS

(75) Inventors: Gregory M. Gilleland, Madison, GA (US); Judy L. Turner, Decatur, IL (US); Penelope A. Patton, Decatur, IL (US); Michael D. Harrison, Decatur, IL (US)

(73) Assignee: A. E. Staley Manufacturing Co., Decatur, IL (US)

( * ) Notice: Subject to any disclaimer, the term of this patent is extended or adjusted under 35 U.S.C. 154(b) by 40 days.

This patent is subject to a terminal disclaimer.

(21) Appl. No.: 09/792,910

(22) Filed: Feb. 26, 2001

(65) Prior Publication Data

US 2002/0142031 A1 Oct. 3, 2002

Related U.S. Application Data

(63) Continuation-in-part of application No. 09/585,846, filed on Jun. 1, 2000, now Pat. No. 6,528,088.

(51) Int. Cl.$^7$ .................................................. A61K 9/36
(52) U.S. Cl. ........................ 424/479; 424/474; 424/475; 424/476; 424/443; 424/451
(58) Field of Search .............................. 424/451, 463, 424/474, 439, 484, 485, 488, 452, 475, 476, 479, 443; 514/777, 778

(56) References Cited

U.S. PATENT DOCUMENTS

| | | | |
|---|---|---|---|
| 2,802,000 A | 8/1957 | Caldwell et al. | 260/233.3 |
| 2,813,093 A | 11/1957 | Caldwell et al. | 260/233.3 |
| 2,825,727 A | 3/1958 | Caldwell | 260/233.3 |
| 3,058,827 A | 10/1962 | Graham | 96/111 |
| 3,329,509 A | 7/1967 | Julius | 99/171 |
| 3,499,962 A | 3/1970 | Wurzburg et al. | 424/35 |
| 3,607,394 A | 9/1971 | Germino et al. | 127/32 |
| 3,865,603 A | 2/1975 | Szymanski et al. | 106/130 |
| 4,009,291 A | 2/1977 | Mitchell et al. | 426/548 |
| 4,026,986 A | 5/1977 | Christen et al. | 264/205 |
| 4,129,134 A | 12/1978 | Hind et al. | 131/2 |
| 4,231,803 A | 11/1980 | Bovier et al. | 106/213 |
| 4,600,439 A | 7/1986 | Schneider et al. | 106/139 |
| 4,615,897 A | 10/1986 | Brown et al. | 426/576 |
| 4,632,848 A | 12/1986 | Gosset et al. | 427/154 |
| 5,360,845 A | * 11/1994 | Billmers et al. | 524/51 |
| 5,451,673 A | 9/1995 | Fishman et al. | 536/123 |
| 5,726,068 A | 3/1998 | Maskasky | 430/569 |
| 6,066,368 A | 5/2000 | Billmers et al. | 427/393.4 |
| 6,375,981 B1 | * 4/2002 | Gilleland et al. | 424/452 |
| 2002/0081331 A1 | 6/2002 | Tanner et al. | 424/451 |

FOREIGN PATENT DOCUMENTS

| | | |
|---|---|---|
| EP | 0 471 558 A2 | 2/1992 |
| EP | 0 547 551 A1 | 6/1993 |
| EP | 0 169 319 B1 | 8/1993 |
| EP | 0 408 503 B1 | 6/1994 |
| EP | 0 409 782 B1 | 6/1994 |
| EP | 0 409 788 B1 | 6/1994 |
| EP | 0 761 691 | 3/1997 |
| EP | 1 038 521 | 9/2000 |
| GB | 1004027 | 9/1965 |
| WO | WO94/25493 | 11/1994 |
| WO | WO97/49762 | 12/1997 |
| WO | WO00/10538 | 3/2000 |
| WO | WO00/18835 | 4/2000 |
| WO | WO01/03677 | 1/2001 |
| WO | WO01/37817 | 5/2001 |
| WO | WO01/91721 | 12/2001 |

OTHER PUBLICATIONS

PCT/US01/14887 International Search Report (Dec. 6, 2001).
Patent Abstracts of Japan No. 05098221 (Apr. 20, 1993).
WO/US01/14978 International Search Report (Mar. 6, 2002).
Arvanitoyannis et al., "Edible Films Made From Sodium Caseinate, Starches, Sugars or Glycerol. Part 1," *Carbohydrate Polymers* 31:179–192 (1996).
Lourdin et al., "Influence of Amylose Content on Starch Films and Foams," *Carbohydrate Polymers* 27:261–270 (1995).
Arvanitoyannis et al., "Edible Films Made From Hydroxypropyl Starch and Gelatin and Plasticized by Polyols and Water," *Carbohydrate Polymers* 36:105–119 (1998).
Arvanitoyannis et al., "Biodegradable Films Made From Low–Density Polyethylene (LDPE), Rice Starch and Potato Starch for Food Packaging Applications: Part 1," *Carbohydrate Polymers* 36:89–104 (1998).
Psomiadou et al., "Edible Films Made From Natural Resources; Microcrystalline Cellulose (MCC), Methylcellulose (MC) and Corn Starch and Polyols—Part 2," *Carbohydrate Polymers* 31:193–204 (1996).
Shih, "Effects of Additives on the Development of Edible Films," *Chemistry of Novel Foods*, Chapter 14, pp. 179–186 (1995).
Kester et al., "Edible Films and Coatings: A Review," *Food Technology* 40:47–59 (1986).
Krochta et al., "Edible and Biodegradable Polymer Films: Challenges and Opportunities," *Food Technology* 51:61–74 (1997).
"Scotchban(TM) Paper Protector, 3M(TM)," 3M Product Information, *World Wide Web at* http://www.3m.com/product/index_S/index_S_287.html.

* cited by examiner

*Primary Examiner*—Thurman K. Page
*Assistant Examiner*—L. Dinda Baron
(74) *Attorney, Agent, or Firm*—Williams, Morgan & Amerson, P.C.

(57) ABSTRACT

Film-forming compositions are disclosed that can comprise, on a dry solids basis, 25 to 75 percent by weight of certain starch derivatives and 25 to 75% primary external plasticizer. The starch derivatives can be chemically modified starches that range in molecular weight from 100,000 to 2,000,000. The high levels of plasticizer in the films give excellent film flexibility and integrity. The films are also resistant to penetration by water, oil and/or grease.

17 Claims, No Drawings

HIGHLY FLEXIBLE STARCH-BASED FILMS

This is a continuation in part of U.S. application Ser. No. 09/585,846 filed on Jun. 1, 2000, U.S. Pat. No. 6,528,088.

BACKGROUND OF THE INVENTION

This invention relates to starch compositions useful in forming flexible films. More particularly, it relates to film-forming compositions containing starch in combination with certain plasticizers.

Gelatin is a protein that forms thermo-reversible films. Gel masses composed of gelatin and a plasticizer such as glycerin are formulated to be liquid above room temperature, form a film when cast on a cooled surface, and re-melt when exposed to higher temperatures again. This ability to re-tackify enables encapsulation of liquid materials in gelatin soft capsules. Films formed from plasticized gelatin set very quickly and have high wet film strength. They are also very elastic with good clarity. Plasticized gelatin also has a relatively low viscosity, even when used at high solids concentrations. In addition, when gelatin is in the presence of water at room temperature, it swells but does not go into solution until heat is applied.

Although gelatin is useful in soft gel applications because of its rapid gelling ability, excellent film forming properties, and ability to impart oxygen impermeability, it has the disadvantages of high cost, limited availability, non-kosher status for food products and, at times, batch property variations. Because of these shortcomings, those industries where the need for gelatin is greatest have long sought means for replacing gelatin.

A number of food and industrial applications would benefit by an inexpensive and readily available structural material from a renewable resource, particularly one that is edible and/or biodegradable. Applications such as agricultural mulch, food packaging, and soft and hard gel capsules for cosmetics, pharmaceuticals and paintballs, need a material that is both strong and flexible under a range of use conditions. Applications such as adhesives, coatings, and caulkings do not have the rigorous strength requirements of free-standing films, but lack of brittleness can be just as important.

Starch meets many of the above requirements, and is an attractive raw material for these applications. Its tendency to brittleness, however, has generally blocked its use in these areas.

There have been some previous reports of plasticized starch films. Lourdin (D. Lourdin, G. D. Valle, P. Colonna, Carbohydrate Polymers 27 (1995) 261–270) incorporated up to 20% glycerol in starch films, but found that their mechanical properties were far inferior to those of synthetic film formers. They found that increasing the amylose content of the starch improved tensile strength. Arranitoyannis (Carbohydrate Polymers 36 (1998) 105–119) measured moderately high tensile values on starch films containing up to 25% polyhydric alcohols. When the plasticized films were oven dried to less than 6% moisture content, they became extremely brittle. Incorporating 15% hydroxypropyl units onto the starch molecules improved film flexibility. Shih (F. F. Shih, in "Chemistry of Novel Foods", A. M. Spanier, M. Tamura, H. Okai, O. Mills, eds., Allured Pub. Corp., Carol Stream, Ill., Ch. 14, pp 179–186) reported tensile values on starch films containing up to 25% plasticizer, but reported that unplasticized films were too fragile for instrumental analysis. In general, increasing plasticizer increases film elongation while decreasing modulus and tensile strength.

Other reports of starch-based films include J. D. Christen, U.S. Pat. No. 4,026,986, 1977; J. C. Rankin, I. A. Wolf, H. A. Davis, C. E. Rist, *Industr. Engr. Chem.* 3 (1958), 120–123; I. A. Wolff, H. A. Davis, J. E. Cluskey, L. J. Gundrum, C. E. Rist, *Industr. Eng. Chem.* 43 (1951) 915–919; A. M. Mark, W. B. Roth, C. L. Mehltretter, C. W. Rist, *Food Technol.* 20 (1966), 75–77; W. B. Roth, C. L. Mehltretter, *Food Technol.* 21, (1967), 72–74; L. Jokay, G. E. Nelson, E. L. Powell, *Food Technol.* 21 (1967), 1064–1066; and J. L. Willet, B. K. Jasberg, C. L Swanson in "Polymers from Agricultural Coproducts, eds. M. L. Fishman, R. G. Friedman and S. J. Huange, pp 50–68, Amer. Chem. Soc., Washington D.C. These films are reported to be very sensitive to environmental humidity and tend to embrittle in low humidity environments.

Starch has also been included as a component in films containing proteins, such as gelatin, and carbohydrate-based hydrocolloids. Plasticizers are generally added to these systems as well. In most of these systems, starch is a secondary film former; the mechanical properties of the film reflect more strongly the properties of the other polymer(s) in the film. The following illustrates these types of systems. Laurent (L. Laurent, European Patent 0 547 551 A1, 1992), combines 5–40% starch with 5–40% gelatin and 10–40% plasticizer to make flexible, edible films. Arvanitoyannis (I. Arvanitoyannis, E. Psomiadou, A. Nakayama; *Carbohydrate Polymers* 31, (1996) 179–192) developed edible films containing starch and sodium caseinate with up to 30% sugar or glycerol. Arvanitoyannis (I. Arvanitoyannis, A. Nakayama, S. Aiba, *Carbohydrate Polymers* 36 (1998) 105–119) developed edible films composed of starch and gelatin with up to 25% polyol plasticizer. Psomiadou (E. Psomiadou, I. Arvanitoyannis, N. Yamamoto; *Carbohydrate Polymers* 31 (1996) 193–204) studied films composed of starch, microcrystalline cellulose and methylcellulose containing up to 30% polyol plasticizers.

Certain films, such as coated paper or coated cardboard, are used in applications where resistance to penetration by water, oil or grease is important. Dog food bags are one example of such an application. Starch-based coatings have potential for such uses, but their tendency to be brittle has presented a major obstacle.

There is a long-standing need for improved film-forming compositions that do not have the shortcomings of prior art compositions.

SUMMARY OF THE INVENTION

One aspect of the present invention is a gelatin-free film-forming composition that comprises starch material and a primary external plasticizer. The starch material is selected from the group consisting of modified starch and waxy starch, and has a dextrose equivalent (DE) of less than about 1, and preferably has no measurable DE (using the Lane-Eynon method). The weight ratio of plasticizer to starch material in the composition preferably is at least 0.5:1, more preferably is from about 0.5:1 to about 3:1, and most preferably is from about 1:1 to about 3:1. This composition optionally may include, in addition to starch and plasticizer, gums, hydrocolloids, synthetic polymers, and/or other additives, but is preferably free of protein. "Gelatin-free" and "protein-free" are used herein to mean that no more than trace amounts (e.g., no more than about 0.1 weight percent on a dry solids basis) of the listed material is present in the composition. Of course, there will often be protein present in the base starch itself. "Protein-free" and similar terms are used herein to mean that substantially no protein (e.g., no more than about 0.1 percent by weight of the total solids in the composition) is added to the composition beyond what that is inherently present in the starch.

The composition can be prepared with water, and preferably has a solids concentration of about 30–70%. (All composition percentages given herein are by weight unless otherwise stated.) In one preferred embodiment of the invention, the solids in the composition comprise 25–50% starch material and 50–75% plasticizer.

The starch material preferably comprises starch that has been chemically modified with a monoreactive moiety to a degree of substitution of at least about 0.015. In a particularly preferred embodiment, the starch material is selected from the group consisting of ether and ester derivatives of starch, such as hydroxypropyl, hydroxyethyl, succinate, and octenyl succinate starch. One specific embodiment of the invention comprises hydroxypropylated potato starch having a degree of substitution of about 0.015–0.30 and a molecular weight of about 200,000–2,000,000. Another specific embodiment of the invention comprises hydroxyethylated corn starch having a degree of substitution of about 0.015–0.3 and a molecular weight of about 200,000–2,000,000. Another specific embodiment of the invention comprises hydroxypropylated high-amylose corn starch with a degree of substitution of 0.015–0.3 and a molecular weight of about 200,000–2,000,000.

In some embodiments of the invention, one or more water soluble gums are added to the mixture of starch and plasticizer. The gum is preferably 0–15% of the total solids in the mixture. The gum preferably is selected from the group consisting of carrageenan, locust bean, xanthan, gellan, agar, alginates, guar, gum arabic, and pectin. A combination of kappa carrageenan and iota carrageenan, most preferably in a weight ratio of about 1:1, is especially preferred.

In another embodiment of the invention, water soluble synthetic polymers may be added to the starch and plasticizer mixture. The synthetic polymer is preferably 0–50% of the total solids in the mixture. The preferred synthetic polymer is polyvinyl alcohol.

In another embodiment of the invention, organic or inorganic filler or pigment particles can be added. The pigments may be chosen from a list including clays, calcium carbonate, titanium dioxide, and synthetic organic pigments.

Industrial plasticizers are discussed in the Encyclopedia of Chemical Technology, $4^{th}$ ed., Vol. 19, pp 258–280, 1997. A plasticizer is a substance which, when added to another material, increases the softness and flexibility of that material. Without being bound by theory, it is believed that plasticizers increase flexibility of polymeric materials by increasing the free volume within the material. Randomly distributed within the material and interspersed among the polymer chains, the plasticizer molecules interfere with the polymer's ability to align its chains and pack into ordered structures. Molecular ordering increases the density of the material (decreases free volume) and impedes mobility of the polymer chains within the material. The increase in free volume imparted by the plasticizer allows room for chain segments to move. The material can then more readily accommodate an applied force by deforming.

Polymers can be plasticized in two general ways: "internally" and "externally." Internal plasticization can occur, for example, through the incorporation of a variety of chemical moieties along the starch molecular chains through ether or ester linkages. These moieties include but are not limited to: hydroxypropyl, hydroxyethyl, carboxymethyl, succinyl and octenylsuccinyl, to name a few. An irregular array of substituents along the polymer backbone prevents close and regular chain packing, and increases free volume in the material.

External plasticizers are relatively small molecules that are miscible with the polymer, and impede chain alignment. External plasticizers are of two distinct classes: primary and secondary. Primary plasticizers are effective in modifying the mechanical properties of the material on their own. Secondary plasticizers may be incompatible, or ineffective, at plasticizing the material on their own, but when added in combination with the primary plasticizer, can be very effective. They are sometimes called "extenders."

The plasticizers required in this invention are primary, external plasticizers, such as sugars and low molecular weight polyols. The properties of the composition optionally can be further enhanced by using internal and/or secondary external plasticizers. A suitable secondary external plasticizer is water. The polyhydric alcohols are hygroscopic; their presence in the starch compositions increases the water content relative to an un-plasticized starch.

Preferred plasticizers for use in the present invention have the general formula $C_nO_nH_x$, wherein n has a value between 3 and 6, and x has a value between 2n and (2n+2), where at least 80% of the oxygen is in the form of hydroxyl groups, and the remaining are in the form of ether groups. This group of preferred plasticizers also includes dimers, disaccharides and low molecular weight (e.g., 300–1800 MW) oligosaccarides of these compounds, and may also include ether or ester derivatives of these compounds. Particular examples of suitable plasticizers include glycerol, diethylene glycol, sorbitol, sorbitol esters, maltitol, sucrose, fructose, invert sugars, corn syrup, and mixtures of one or more of these.

In preparing the films described in this invention, the mixture of starch and water is heated with stirring to hydrate fully all components in the mixture. The hydration of starch by heating is termed "cooking." The preferred conditions for cooking the starch mixture are 80–200° C. for 5–60 minutes. Those versed in the art of starch cooking will recognize that a variety of cooking techniques may be employed, including but not limited to, open kettles or high-pressure jet cookers. In another embodiment of the invention, instant, pre-gelled or cold-water swelling starches may be used. For these starches, it is not required that the mixture be heated to hydrate fully the starch.

The plasticizer, may be, but is not required to be, mixed with the starch and water prior to cooking. The gum, synthetic polymer, or other components of the film-forming mix, may be, but are not required to be, mixed with the starch and water prior to cooking. Whether or not the non-starch components are mixed with the starch and water prior to cooking will depend on a number of considerations, including the hydration requirements of the other components, their thermal stability, viscosity constraints, and convenience.

Another aspect of the invention is a flexible adhesive for paper tape and other paper-based articles comprised of the above-described starch-based composition, usually with much of the water removed. Yet another aspect of the invention is a flexible paper coating comprised of the above-described composition. Yet another aspect of the invention is a flexible coating in which the starch-based composition is a film-forming component, but which may also include fillers or pigments, latex emulsions or other additives.

Another aspect of the invention is a flexible material that resists penetration by grease and oil. The material comprises a flexible substrate and a coating thereon. The coating comprises the above-described starch-based composition. Preferably the substrate is substantially planar and comprises two surfaces, with the coating being located on at least one of the surfaces. For example, the substrate can be a flat sheet of paper or cardboard. "Substantially planar" in this context means that the substrate can be configured generally in a single plane, but may have minor deviations from that configuration (e.g., a sheet of corrugated cardboard).

Another aspect of the invention is a flexible material that resists penetration by water. The material comprises a flexible substrate and a coating thereon. The coating comprises the above-described starch-based composition. Preferably the substrate is substantially planar and comprises two surfaces, as described above, such as a sheet of paper or cardboard. The coating is located on at least one of the surfaces.

Another aspect of the invention is an edible film that comprises the above-described starch-based composition, usually with much of the water removed. Yet another aspect of the invention is a soft gel capsule that comprises a sealed capsule wall and a first substance that is encapsulated by the sealed capsule wall. The capsule wall comprises the above-described starch-based composition. In one embodiment of the invention, the film or the capsule wall consists essentially of the combination of starch material and plasticizer.

The first substance encapsulated by the capsule wall can be any of a variety of materials that have been encapsulated by gelatin in the past. Many such substances are edible, including drugs, vitamins, nutritional supplements, and premeasured food ingredients such as flavorings. It can also comprise, for example, photographic or dye solutions.

Another aspect of the invention is a method of encapsulating a first substance. This method comprises the steps of providing a first substance and an edible film as described above, and encapsulating the first substance in the film. Preferably, the film used in this method has been formed on a surface having a temperature of at least about 100° F.

In one preferred embodiment of the invention, the film or capsule wall consists essentially of the combination of starch material, plasticizer, and optionally gum.

The present invention provides an economical alternative to the synthetic polymers currently used to impart dimensional stability and binding strength in adhesives and industrial coatings. It also provides an economical means for replacing gelatin in compositions utilized in the production of soft gel or hard shell capsules, or gel-coated tablets for food, pharmaceutical, and industrial applications. Further, the starch-based materials of this invention are compatible with existing application equipment used for manufacture of tapes, coated papers, and various products that in the past have been primarily comprised of gelatin.

In compositions of the present invention, the starch, plasticizer, and any other solid ingredients preferably make up from about 30 to 70% by weight of an aqueous slurry. Flexible films are prepared by blending together the starch, plasticizer, and water, and heating the mixture to a temperature and for a time sufficient to gelatinize the starch fully, (e.g., 80–200° C. for 5–60 min). Additional materials may be added to the mixture of starch and plasticizer in order to impart improved functionality. These materials may be added before or after heat treatment. The mixture is then sheeted, while warm or hot, to form a thin film. The mixture may be sheeted directly onto paper, board or other surface when used as a coating or adhesive, or onto a casting surface from which the cooled film can be lifted and transfer to rolls, or to fabrication equipment.

The present invention has a number of benefits. Starch is a low cost and readily available material. The starch may be modified using a number of chemical and physical means to enhance its properties while maintaining its status as a material approved as a food additive by the FDA. It may be subjected to a number of additional modifications while maintaining its FDA acceptability for use in contact with foods. It is biodegradable. It is water soluble and therefore does not require expensive, hazardous and/or volatile solvents that many other polymers require for processing. A range of materials are available for plasticizing starch which are both inexpensive and FDA approved for food use. In addition, the compositions of the present invention can be cooked more easily than the high amylose compositions that have been used in the past.

A film comprising the above-described composition can function as a pressure sensitive adhesive. The combination of a high plasticizer content and a highly substituted starch plasticizes the film to the point of providing tack through a broad humidity range.

DETAILED DESCRIPTION OF SPECIFIC EMBODIMENTS

Examples of modified starches that can be used in the present invention include non-retrograding starches derived by chemical modification of starch from any plant source, including corn, waxy maize, potato, sweet potato, wheat, rice, sago, tapioca, sorghum, high amylose corn, and the like. The particular starch chosen will depend on its performance, availability, and cost. Among the useful modified starches are the common ether and ester derivatives of starch, including but not limited to hydroxypropyl, hydroxyethyl, succinate, and octenyl succinate starch derivatives. Because waxy starches do not retrograde, they are suitable for use without derivatization. Also included among the modified starches suitable for use in the practice of this invention are the thermally converted, fluidity or thin boiling type products derived from the aforementioned types of chemically modified starches. Such materials may be of lower molecular weight, prepared by heating the modified starch alone or by subjecting the starch to a hydrolytic acid and/or heat treatment, or by any other known method designed for the thermal conversion of the starch, such as enzymic heat treatment.

Preferred modified starches are the hydroxyethyl derivatives of dent corn starch and the hydroxypropyl derivatives of potato starch, each preferably having a degree of substitution from 0.015–0.30 ds and a molecular weight of from 100,000 to 2,000,000. In the case of waxy starches of corn, potato, etc., the branches of the amylopectin replace the function of the ether or ester substituents; these starches are functional in the present invention without additional chemical modification, although their properties are not impaired by additional modification, and are enhanced by molecular weight reduction.

Suitable plasticizers include, but are not limited to, glycerol, sorbitol, maltitol, fructose, sucrose, corn syrup, and mixtures thereof.

A variety of optional ingredients may be incorporated into the starch compositions of this invention, before, during, or after cooking the starch. Among the suitable materials that may be utilized are gums, synthetic polymers, preservatives, colorants, clays, pigments, flavoring agents, hardeners, antifoggers, sensitizers, and spreading agents. The inclusion of such additives has no adverse effect upon the properties exhibited by the novel starch-based compositions of the present invention.

Suitable hydrocolloid gums include carrageenan, locust bean gum, xanthan gum, gellan gum, agar, alginates, guar gum, gum arabic, cellulosic derivatives and pectin. Suitable synthetic polymer additives include polyvinyl alcohol, polyethylene glycol, polyacrylamide and polyethylene oxide, and certain derivatives of these polymers.

A composition of the present invention is formed by combining the dry solids (i.e., the modified starch or waxy starch, plasticizer, and any other additives), slurrying in water, and heating at a temperature and for a time sufficient to hydrate the starch, and other gums if necessary. Optionally, this can take place under a vacuum or high pressure. Films can be formed from these starch-based compositions by any conventional method designed to solubilize and deposit a continuous coating or layer of the solution onto a substrate or mold of any form. Among the suitable coating techniques are spraying, dipping, air knife, trailing blade, reverse and direct roll coaters, etc. A film, such as an overcoating or capsule shell, may then be formed by drying the coated solution to a desired moisture content, using any means suitable for the particular purpose. Suitable conventional means include heated rollers, warm or cold air impingement, low humidity chamber or oven drying, etc. For example, during paper coating, the coated sheet is passed over steam-heated rolls to drive moisture from the coating.

EXAMPLES

The invention will be further illustrated by, but is not intended to be limited to, the following examples.

Compositions were prepared containing the component amounts given in Examples 1–3, on a dry basis. The relative starch molecular weight is reflected in the grams starch needed to give 1000 cps viscosity at 35° C., 160 rpm, using a Rapid Visco Analyzer (Model RVA-4D, Foss Food Technology, Eden Prairie, Minn.) (hereafter referred to as "RVA"). In Examples 1–3, the starch, fructose, and sufficient water to give total sample weight of 1000 g, were mixed together in a beaker. The slurry was then cooked using a bench-top jet cooker at 260–270° F., 3.5 gal/min flow rate, and tail pipe residence time of 20 sec. The cooked starch pastes were collected in glass beakers, covered tightly with foil, and placed in a 85° C. water bath until needed.

Example 1

230 g starch containing 2% hydroxyethyl substitution, acid hydrolyzed to give a viscosity of 1000 cps at 15% cooked paste solids 230 g crystalline fructose sufficient water to give 1000 g slurry

Example 2

180 g starch containing 2% hydroxyethyl substitution, acid hydrolyzed to give a viscosity of 1000 cps at 10% cooked paste solids 270 g crystalline fructose sufficient water to give 1000 g slurry

Example 3

150 g starch containing 2% hydroxyethyl substitution, acid hydrolyzed to give a viscosity of 1000 cps at 10% cooked paste solids 300 g crystalline fructose sufficient water to give 1000 g slurry Pre-weighed sheets of 23 lb/3000 ft$^2$ base paper were coated with the starch pastes using a #10 draw-down rod, to give a coating pick-up of 16 lb/3000 ft$^2$. A top sheet of 23 lb/3000 ft$^2$ paper was placed on top of the wet starch coating, and smoothed into place by drawing a dry draw-down rod over the top. The finished tapes were allowed to air dry overnight.

The tapes were cut into 7 mm×70 mm strips, and their tensile strengths measured using a Stable Microsystems TA-XT2 Texture Analyze equipped with jaw clamp attachments. Ten tests were run on each tape, in both the machine and cross directions, and the results averaged.

Table 1 summarizes the results. Included in the table are tests run on tape prepared from the same base paper and 16 lb/3000 ft$^2$ amorphous polypropylene as the tape laminate. It can be seen that the starch-based adhesives impart as much tensile strength to the tape while greatly increasing the extensibility of the tape. The control tapes are brittle and break at a very low elongation. With the plasticized starch, the extension to break is increased by as much as a factor of 3.

TABLE 1

Effect of plasticized starch laminate on tensile strength and plasticity of tape, compared with a standard amorphous polypropylene laminate

| Tape adhesive | Starch: Plasticizer | Extension to Break | | Force to Break, lbs/in | |
|---|---|---|---|---|---|
| | | avg | st dev | avg | st dev |
| | | Machine Direction | | | |
| none - 2× base paper | — | 1.1% | 0.2 | 55 | 3 |
| amorphous polypropylene | — | 1.5% | 0.2 | 57 | 3 |
| Example 1 | 1:1 | 2.1% | 0.4 | 62 | 6 |
| Example 2 | 1:1.5 | 2.5% | 0.1 | 58 | 2 |
| Example 3 | 1:2 | 2.1% | 0.2 | 53 | 3 |
| | | Cross Direction | | | |
| none - 2× base paper | — | 3.1% | 0.4 | 18 | 1 |
| amorphous polypropylene | — | 4.4% | 1.2 | 22 | 2 |
| Example 1 | 1:1 | 4.6% | 1.4 | 21 | 2 |
| Example 2 | 1:1.5 | 6.2% | 1.0 | 21 | 2 |
| Example 3 | 1:2 | 6.1% | 0.6 | 20 | 1 |

Examples 4–9 illustrate the effects of plasticizers, in their various forms, on film flexibility. The plasticizer in these formulations is fructose. It is an external, primary plasticizer. Hydroxypropyl units added to the starch molecular chains act as internal plasticizers. Fructose is hygroscopic, and, in high relative humidity, facilitates the uptake of moisture into the starch films. The water acts as a secondary, external plasticizer. The relative contributions of each can be seen by comparing the flexibility rating of the films.

The compositions of Example films 4–9 are listed in Table 2. All starches had weight average molecular weights of 600,000. Starch moistures ranged from 9–11%. To prepare the films, the starch, plasticizer and water were mixed together in the cup of an RVA, and heated, using 160 rpm stirring, to 98° C. over 4.5 minutes. The mixture was held at 98° C., with continued stirring, for 6.5 minutes, then transferred to a smooth surface and drawn into a film of 0.5 mm thickness using a draw-down bar. They were allowed to set, then aged overnight at the relative humidity conditions indicated in Table 2. Their relative flexibilities were then evaluated by bending the films. Films which shattered with little force were given a flexibility rating of zero. Films which were flexible and pliant upon bending were given a rating of ten. These results are given in Table 3.

TABLE 2

Compositions of Example Film Formulations

| Example # | % HP on Starch | Starch weight (g) | fructose (g) | Water (g) | slurry solids, % | Plasticizer/ Starch | % Relative Humidity |
|---|---|---|---|---|---|---|---|
| 4 | 2 | 11.6 | 2.1 | 21.4 | 35 | 0.2 | 55 |
| 5 | 2 | 9.4 | 7.5 | 18.1 | 45 | 0.9 | 55 |
| 6 | 2 | 6.6 | 11.8 | 16.6 | 50 | 2 | 55 |
| 7 | 0 | 10.7 | 8.4 | 16.0 | 50 | 0.9 | 55 |
| 5 | 2 | 9.4 | 7.5 | 18.1 | 45 | 0.9 | 55 |
| 8 | 4.9 | 9.9 | 8.4 | 16.7 | 50 | 0.9 | 55 |
| 5 | 2 | 9.4 | 7.5 | 18.1 | 45 | 0.9 | 55 |
| 9 | 2 | 9.4 | 7.5 | 18.1 | 45 | 0.9 | 25 |

TABLE 3

Flexibility Ratings of Example Films

| Film # | Plasticizer/ Starch | % HP on Starch | % Relative Humidity | Flexibility rating |
|---|---|---|---|---|
| 4 | 0.2 | 2 | 55 | 0 |
| 5 | 0.9 | 2 | 55 | 5 |
| 6 | 2 | 2 | 55 | 8 |
| 7 | 0.9 | 0 | 55 | 0 |
| 5 | 0.9 | 2 | 55 | 5 |
| 8 | 0.9 | 4.9 | 55 | 10 |
| 5 | 0.9 | 2 | 55 | 5 |
| 9 | 0.9 | 2 | 25 | 3 |

The film analyses of Table 3 are divided into 3 sections. The first section compares the effect of level of plasticizer. A plasticizer/starch ratio of 0.2/1 yielded a very brittle films which shattered with little force. Increasing plasticizer increases flexibility. The second group of results in Table 3 compare the effect of hydroxypropyl substitution on starch. A surprising aspect of this invention is the large effect of starch substitution on film flexibility. While the 4.9% HP groups on starch comprise only about 2.7% of film solids, they render a more flexible film than one containing 67% fructose plasticizer. The third section of Table 3 compares the effect of atmospheric humidity on film flexibility. The plasticizers of this invention are hygroscopic and draw moisture from the air into the film. This moisture acts as a secondary external plasticizer. It contributes to the effect of the primary plasticizer, increasing plasticization. It should be noted that conventional starch films containing 5–30% plasticizer are reported to be extremely sensitive to relative humidity. These films of this invention vary in flexibility with variations in humidity, but remain flexible. They are not embrittled by low atmospheric humidity.

Examples 10–16 illustrate the effect of film composition on the properties of viscosity, rate of film formation and film strength. Compositions were prepared containing the component amounts given in examples 10–16 on a dry solids basis.

Example 10

5.2 g potato starch, substituted with 3 wt % hydroxypropyl groups and of 600,000 molecular weight 0.75 g kappa carrageenan 9.7 g Sorbitol Special (obtained from SPI Polyols, New Castle, Del.)

Example 11

8.4 g potato starch, substituted with 0.5% hydroxypropyl groups and of 600,000 molecular weight 11.8 g Sorbitol Special Example 12

8.4 g potato starch, substituted with 3.0% hydroxypropyl groups and of 600,000 molecular weight 11.8 g Sorbitol Special 0.5 mm thickness.

Example 13

5.2 g potato starch, substituted with 3 wt % hydroxypropyl groups and of 600,000 molecular weight 0.75 g gellan 9.7 g sorbitol 0.5 mm thickness.

Example 14

5.2 g waxy corn starch of 800,000 molecular weight 0.75 g kappa carrageenan 9.7 g sorbitol Example 15

5.2 g potato starch, substituted with 3 wt % hydroxypropyl groups and of 600,000 molecular weight 0.75 g kappa carrageenan 9.7 g glycerine

Example 16

5.2 g potato starch, substituted with 3 wt % hydroxypropyl groups and of 600,000 molecular weight 0.75 g kappa carrageenan 9.7 g Sorbitol Special Sufficient 1% NaCl to bring to 35 g total mass.

Starch molecular weights were measured by gel permeation chromatography and weight averaged. Starch viscosities are measured using an RVA. In Examples 10–16, the starch, plasticizer, and gum, if used, were mixed with sufficient deionized water (except where indicated) to give a total slurry mass of 35 g. The components were mixed together in the cup of the RVA, and heated, using 160 rpm stirring, to 98° C. over 4.5 minutes. The mixture was held at 98° C., with continued stirring, for 6.5 minutes, then transferred to a chilled surface and drawn into a film of 0.5 mm thickness for film testing. A second paste of the same composition was cooked in the same way and then transferred into a pre-heated glass jar, tightly capped, and placed into an oven for pot life evaluations.

In particular, in Examples 10–16, the film samples were prepared by casting a layer of the test solution at about 180° F. (82° C.) onto a Teflon-coated piece of glass (approximately 9 in×13 in). The bottom of the glass was in contact with circulating cold water so that the surface temperature of the glass was 52° C. The film was formed by pouring the hot paste onto the Teflon surface and then quickly drawing the paste across the glass using a Bird Applicator or similar device, the gap width of which could be adjusted to control film thickness. Wet film thicknesses were typically 0.5–0.8 mm. The films were cast, dried, and aged in a room controlled to 70° F. and 25–30% relative humidity.

The viscosity of the starch mixture was measured by the RVA instrument, which records viscosity throughout the cook.

Pot life was evaluated by transferring the hot paste into preheated glass jars with screw lids, and placing these in a 180° F. oven. The fluidity of the mass was evaluated after 2 hours by tipping the jars upside down and assigning a flow rating of 0–5. A mass that flowed with the ease of water was given a rating of 5; a mass which did not flow at all was given a rating of 0. The oven temperature was then lowered by 10° F. and the samples allowed to equilibrate for 2 hours, and then their flow properties re-assessed. The oven was lowered in 10° F. increments until all samples had a flow rating of zero—that is, they had all gelled.

Thermo-reversibility was assessed by reheating the pot life samples, described above, in 10° F. increments, allowing them to equilibrate at each temperature, and then assigning a flow rating using the same criteria as for pot life.

The films were evaluated for rate of filming using a Gardco Electronic Multicycle Circular Drying Time Recorder, and following test method procedure ASTM D 5895. The recorder was placed above the wet film, and a stylus was lowered onto the surface of the film and allowed to rotate for a defined time of 10 minutes. Three points were determined from this test: tack free, dry hard, and dry through. Tack free is defined as the point in the path made by the stylus on the film where the continuous track ends and a discontinuous track or tear begins. Dry hard is the point in the path where the stylus no longer tears the film, and only leaves a visible trace. Dry through is reached when the stylus no longer leaves any visible track on the film.

The tensile strength of the wet film was measured using a Stable Microsystems TA-XT2 Texture Analyzer. To do this, 0.5 in×8 in strips were cut from the wet film 5 minutes after it was cast and these were loaded onto the Texture Analyzer. The tensile test was started 15 minutes after the film was cast.

Film appearance (color and clarity) was evaluated on the basis of visual observation.

The physical properties of the hot starch/plasticizer pastes for Examples 10–16, and the resulting films, are listed below in Table 4.

TABLE 4

| Example number | Peak viscosity during cook, cps | Hot paste final visc, cps, 98° C. | Time until tack free, sec | Time until dry hard, sec | Wet film tensile strength, g force | Pot life rating @ 180° F. | Minimum flowable temp, ° F. | Re-softening temp, ° F. |
|---|---|---|---|---|---|---|---|---|
| 10 | 18000 | 1700 | <5 | <10 | 75 | 3.5 | 160 | 150 |
| 11 | 14000 | 2500 | 65 | 100 | * | | | |
| 12 | 13000 | 1150 | 4020 | 5700 | * | | | |
| 13 | | 2300 | <5 | <10 | 108 | 0.5 | >180 | >180 |
| 14 | 13000 | 2400 | <5 | <10 | 65 | 3.0 | 170 | 150 |
| 15 | 16000 | 1500 | <5 | <10 | 50 | 4.0 | 160 | 150 |
| 16 | 11000 | 1300 | <5 | <10 | 75 | 3.5 | 170 | 150 |

* Too weak to test

Example 17 describes a pressure sensitive adhesive composed of highly substituted starch and high level of plasticizer. The components of Example 17 were mixed together, cooked as described for Examples 1–3, and the film cast onto a glass surface.

Example 17

6.92 g potato starch, 600,000 mol wt, 4.85% hydroxypropyl content, 7.34% moisture 12.96 g glycerine 15.1 g water The film of Example 17 remains tacky for months at humidities ranging from 25% to 55% RH. Paper can be stuck to the adhesive, removed from it, and re-stuck to it without damage to the paper or loss of adhesive tack.

Example 18

Oil and grease resistance was tested on three types of paper that were coated with starch-based flexible films consisting of equal parts by weight acid-degraded, hydroxyethylated dent starch and fructose. The paper was coated using conventional "draw down" techniques. The starch/ fructose pastes typically comprised 20–35% solids with the balance being water. Coating pick-ups were typically 10–12 lb/3300 ft$^2$. The papers that were coated were (1) an unbleached Kraft, (2) a bleached coating base stock and (3) a copy paper. Samples of the bleached and unbleached kraft paper which had been surface treated with 3M's SCOTCH-BAN® fluorocarbons, "807" and "845" were also used.

Each paper—the untreated, flexible film-treated, and fluorocarbon-treated when available —was tested for oil and grease resistance using the following methods:

1. 3M Test Kit For Surface Oil Repellency (a modification of this test has been established as TAPPI Useful Method 557).

Place each test specimen (e.g., sheet of paper) on a clean, flat surface, test side up, being careful not to touch the area to be tested. Drop on the test area, from a height of about 1 inch (2.5 cm), a drop of test solution from an intermediate Kit Number dropping bottle. Start a stop watch as the drop is applied. After exactly 15 seconds, remove excess fluid with a clean swatch of cotton and immediately examine the wetted area. Failure is evidenced by pronounced darkening of the specimen caused by penetration, even in a small area, under the drop. Repeat the procedure as required, making sure that drops from succeeding Kit Number bottles fall in untouched areas. Report results as the Kit Rating, which is the highest numbered solution that stands on the surface of the specimen for 15 seconds without causing failure. Report the average Kit Rating of five specimens to the nearest 0.5 number.

2. Dog Food Test, 10 minutes at 190° F.

Fold test specimen in half. Roll a 500 gram weight over the fold. Open the folded sheet and place on a tray. Using a 50 ml beaker to measure, place ~40 ml of dog food (that contains no less than 20% crude fat) on the test specimen. Place tray in a 190° F. oven for ten minutes. After ten minutes remove the tray from the oven, remove the dog food from the test specimen. Visually evaluate the paper for grease penetration, on a scale from 1 to 10. A score of one indicates complete failure of the surface sizing to repel grease—the sheet is uniformly stained with grease. A score of ten indicates no evidence of any grease being absorbed by the paper.

3. Dog Food Test, 16 hours at 140° F.

Fold test specimen in half. Roll a 500 gram weight over the fold. Open the folded sheet and place on a tray. Using a 50 ml beaker to measure, place ~40 ml of dog food (that contains no less than 20% crude fat) on the test specimen. Place tray in a 190° F. oven for 16 hours. After 16 hours remove the tray from the oven, remove the dog food from the test specimen. Visually evaluate the paper for grease penetration, on a scale from 1 to 10. A score of one indicates complete failure of the surface sizing to repel grease—the sheet is uniformly stained with grease. A score of ten indicates no evidence of any grease being absorbed by the paper.

The table below summarizes the results of this testing. It can be seen that the flexible film-coated paper is equal or superior to the fluorocarbon-treated paper in every case.

The untreated paper was completely saturated by grease at the end of both dog food tests, and it was stained by the lowest number (least aggressive) 3M Kit test solution.

The sheets coated with the flexible film coating, on the other hand, gave excellent grease resistance. Five out of the six dog food tests gave 100% grease hold-out. The sole exception (the bleached coating base sheet at 10 min and 190° F.) stained very slightly so was rated a 9.5. In the 3M Kit Test, all the flexible film-coated paper survived staining by even the most aggressive test solution (solution #12).

In contrast, the fluorocarbons gave complete resistance to the dog food grease only in the unbleached Kraft. The bleached coating stock stained over 50–60%. In the 3M kit test none of the fluorocarbon sheets resisted staining by solvents higher than #9; one was stained by all solvents higher than #4.

TABLE 5

| | | Dog Food Test* | | |
|---|---|---|---|---|
| Paper | Coat Wt lb/3300 ft 2 | 10 min, 190 F. | 16 hr, 140 F. | 3M Kit test** |
| Unbleached Kraft | | | | |
| No surface treatment | none | 1 | 0 | 0 |
| Flourocarbon treated: 807 | N/A | 10 | 10 | 7 |
| Flourocarbon treated: 845 | N/A | 10 | 10 | 4 |
| Flexible film coated | 10–12 | 10 | 10 | 12 |
| Bleached Coating Base | | | | |
| No surface treatment | none | 1 | 0 | 0 |
| Flourocarbon treated: 807 | N/A | 4 | 4 | 9 |
| Flourocarbon treated: 845 | N/A | 5 | 4 | 8 |
| Flexible film coated | 11–14 | 9.5 | 10 | 12 |
| Copy | | | | |
| No surface treatment | none | 1 | 0 | 0 |
| Flexible film coated | 10–12 | 10 | 10 | 12 |

*A rating of 1 indicates complete staining of the paper with grease; 10 indicates no staining.
**The ranking indicates the highest number test solution which the sheet resists without staining. Higher-numbered solutions are more aggressive solvents and predict higher grease resistance.

The starch film coat weights tested in this example are fairly high. Lower coat weights will hold-out grease also. It is preferred that the coating form a continuous, defect-free film. A pin-hole (resulting, for example, from an air bubble) will allow grease and oil to penetrate.

It should be pointed out that the dog food tests call for the coated sheet to be creased, and the dog food placed over the creased area. A typical starch film is brittle and would crack during creasing. Grease would then easily pass through the crack and stain the paper. It is this aspect of the flexible films of the present invention that make them so suitable for this application.

Example 19

Water resistance ("sizing") is a property required of many paper grades. To provide water resistance, chemical additives are added to paper, either during formation of the sheet or by surface application to the sheet after it is formed. The chemicals added during the formation of the sheet are typically hydrophobic, small molecules such as alkyl ketene dimer, and alkenyl succinic anhydride. Surface-applied sizing agents are often low molecular weight, hydrophobic polymers such as polystyrene acrylate.

This experiment tested the ability of paper coated with blends of starch and fructose to resist penetration by water. A 39 lb coating base stock was used, coated with blends of fructose and Ethylex hydroxyethylated dent corn starch (available from Tate & Lyle North America, Decatur, Ill.). All sheets were allowed to equilibrate overnight or longer at 70° F. and 55% RH.

Water resistance testing was performed using a Hercules Sizing Tester (HST) according to TAPPI Test method T530.

Reflectance was set to 70%. Sizing response was defined as the time from addition of 10 ml Hercules green ink to the paper surface until reflectance from the underside of the paper dropped to 70%.

The first comparisons were of sheets coated with flexible starch films containing Ethylex 2075 and fructose, and Ethylex 2025 alone. At similar solids, pastes of Ethylex 2025 and of the Ethylex 2075/fructose blend have similar viscosities. Ethylex 2025 is a typical starch used for size press and coatings.

Table 6 compares time to 70% reflectance (HST response) for untreated paper, paper coated with Ethylex 2025 only, and paper coated with fructose/Ethylex 2075 blended at 0.7/1 ratio. (The higher the HST the greater the water resistance.) The coating pickups for the Ethylex and Ethylex/fructose blends were similar. Ethylex 2025 by itself gave virtually no water resistance, but the plasticized Ethylex 2075 film gave excellent water resistance.

TABLE 6

| starch | fructose/ starch | ct wt lb/ton | HST, sec, avg | st dev |
|---|---|---|---|---|
| none | — | 0 | 0.2 | 0.3 |
| 2025 | 0 | 270 | 0.7 | 0.1 |
| 2075 | 0.7 | 248 | 79 | 7 |

Two plasticizer levels were tested: 0.7 parts and 1.4 parts to 1 part of Ethylex 2075. The lower plasticizer level gave far better water resistance properties. (Table 7).

The coatings were applied to the sheets at two paste concentrations. The water resistance properties of these films was unaffected by the solids concentration of the paste when the coatings were applied to the sheets. (See Table 7).

TABLE 7

The Effect of Plasticizer Level, and Starch Paste Concentration when Coating was Applied, on Water Resistance.

| starch | paste solids | fructose/ starch | ct wt lb/ton | HST, sec, avg | st dev |
|---|---|---|---|---|---|
| 2075 | 17 | 0.7 | 248 | 79 | 7 |
| 2075 | 25 | 0.7 | 266 | 78 | 23 |
| 2075 | 25 | 1.4 | 231 | 38 | 14 |
| 2075 | 17 | 1.4 | 239 | 36 | 7 |

The coated sheets were tested flat and creased. Creasing the sheets had no effect on water resistance. With 0.7 parts plasticizer, the starch/fructose films were flexible enough to withstand creasing without cracking.

Increasing the coat weight of plasticized starch increased water resistance. (The coatings tested contained 0.7 parts fructose and 1 part Ethylex 2075.) A minimum of about 150 lb/ton (about 4.5 lb/3300 ft$^2$) was needed before the coating started imparting water resistance. Beyond that, water resistance increased sharply. This minimum coat weight for water hold-out may reflect a critical overlapping of the polymer chains, and the minimum starch needed for a continuous film.

Water resistance increased with higher coat weights, and the variation in HST response decreased. This decrease in test-to-test variability probably reflects a decrease in the number and severity of film defects as the film thickness increases.

Replacing Ethylex 2075 in the flexible coating with the lower molecular weight Ethylex 2065 starch significantly reduced water resistance (Table 8).

TABLE 8

Effect of Starch Molecular Weight (Ethylex 2075 vs. 2065) on Water Resistance

| starch | fructose/ starch | ct wt lb/ton | HST, sec, avg | st dev |
|---|---|---|---|---|
| 2075 | 0.7 | 248 | 79 | 7 |
| 2065 | 0.7 | 270 | 38 | 25 |

Given the effect of starch molecular weight on water resistance, it seemed plausible that molecular weight alone (rather than the flexible nature of the coating) might explain the lack of water resistance of the Ethylex 2025-coated sheets. To test this possibility, paper was coated with solutions of Ethylex 2075 alone (no fructose). These sheets exhibited significant water holding (Table 9). The average HST responses for the all-Ethylex 2075 coatings and the plasticized Ethylex 2075 coatings, at the same average coat weight, were similar.

The test-to-test variation in the all-Ethylex coatings, however, was large. The standard deviation for 8 tests was 59, compared with only 7 for the plasticized coating.

TABLE 9

Effect of Plasticizer Content on Water Resistance

| starch | fructose/ starch | ct wt lb/ton | HST, sec, avg | st dev |
|---|---|---|---|---|
| 2075 | 0.7 | 250 | 79 | 7 |
| 2075 | 0 | 250 | 64 | 59 |

The data in Table 7 indicate that increasing fructose content in the coating decreases water resistance. However, at 0.7 parts fructose, the water resistance of the coating was as good or better than that of the all-Ethylex coating. To test whether fructose was a functional contributor or simply a diluent, all the coat weights were converted to weights in Ethylex 2075 alone, and those values plotted against HST values. The enhancement of water-resistance by fructose was clear. If the water resistance was due only to the Ethylex, the HST data should have all fallen on the same curve. Instead, the films with no fructose gave the lowest HST values per lb of Ethylex, and the films with the highest fructose gave the highest HST values.

There are several similarities but also some striking dissimilarities among the effects of coating variables on water resistance and grease resistance. Table 10 below summarizes these. For both, increased starch molecular weight and an optimum amount of plasticizer enhance hold-out (i.e., resistance to penetration). This is consistent with a hold-out mechanism based on a strong, continuous flexible film. For grease hold-out, it appears preferable that the film is concentrated within a narrow region of the sheet since the concentration of the starch paste during application is an important variable for performance. However, there appears to be no effect of the film "location" or "density" for water resistance. This may be because of the chemical similarity between starch and the cellulose fibers. On the other hand, once a film of adequate thickness is formed on the sheet, grease hold-out does not improve with increasing starch film thickness (coat weight), whereas, beyond this minimum amount, water resistance increases with coat weights up through 600 lb/ton. Creasing the coated sheets can lead to failure of the grease-resistant film. Without being bound by theory, it is believed that cracks can form in the film during creasing which provide a channel for grease to penetrate. No effect of creasing on water penetration was observed, regardless of plasticizer level.

TABLE 10

Comparison of Plasticized Starch Variables on Water and Grease Resistance of Coated Paper

| Increasing Variable | Grease Resistance | Water Resistance |
| --- | --- | --- |
| Starch Mol Wt | increases | increases |
| Parts fructose above 0.7 | decreases | decreases |
| Flexible starch coat wt | no effect | increases |
| Starch paste solids | increases | no effect |
| Creasing the sheet | decreases | no effect |

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A gel coated tablet comprising:
    a sealed capsule wall and a first substance that is encapsulated by the sealed capsule wall;
    wherein the capsule wall comprises a composition comprising (a) starch material having a dextrose equivalent less than about 1 and selected from the group consisting of modified starch and waxy starch and (b) a primary external plasticizer, wherein the weight ratio of plasticizer to starch material is at least about 0.5:1.

2. A material resistant to penetration by at least one of grease, oil, and water, comprising a flexible substrate and a coating thereon, the coating comprising (a) starch material having a dextrose equivalent less than about 1 and selected from the group consisting of modified starch and waxy starch, wherein the starch material comprises starch (i) which has been chemically modified with a monoreactive moiety to a degree of substitution of between 0.015 and 0.3 and (ii) which has an average molecular weight of between about 100,000 and 2,000,000, and (b) a primary external plasticizer, wherein the weight ratio of plasticizer to starch material is at least about 0.5:1.

3. The material of claim 2, wherein the substrate is substantially planar and comprises two surfaces, with the coating being located on at least one of the surfaces.

4. The material of claim 3, wherein the substrate comprises a sheet of paper or cardboard.

5. The material of claim 2, wherein the weight ratio of plasticizer to starch material is from about 0.5:1 to about 3:1.

6. The material of claim 5, wherein the weight ratio of plasticizer to starch material is from about 1:1 to about 3:1.

7. The material of claim 5, wherein the weight ratio of plasticizer to starch material is about 0.7:1.

8. The material of claim 2, wherein the coating is protein-free.

9. The material of claim 7, wherein the coating consists essentially of starch material and plasticizer.

10. The material of claim 8, wherein the coating comprises 25–75% starch material, 25–75% plasticizer, and 0–15% gum or synthetic polymer.

11. The material of claim 2, wherein the starch material is selected from the group consisting of ether and ester derivatives of starch.

12. The material of claim 11 wherein the starch material is selected from the group consisting of hydroxypropyl, hydroxyethyl, succinate, and octenyl succinate starch.

13. The material of claim 2, wherein the starch material comprises waxy starch.

14. The material of claim 2, wherein the plasticizer comprises at least one polyol.

15. The material of claim 2, wherein the plasticizer comprises at least one compound having the formula $C_nO_nH_x$, wherein n has a value between 3 and 6, and x has a value between 2n and (2n+2), or a dimer or oligomer of such a compounds.

16. The material of claim 2, wherein the plasticizer is selected from the group consisting of glycerol, sorbitol, maltitol, fructose, sucrose, corn syrup, and mixtures thereof.

17. A material resistant to penetration by at least one of grease, oil, and water, comprising a flexible substrate and a coating thereon, the coating comprising (a) starch material having a dextrose equivalent less than about 1 and selected from t e group consisting of hydroxypropyl, hydroxyethyl, succinate, and octenyl succinate starch, wherein the starch material comprises starch (i) which has been chemically modified with a monoreactive moiety to a degree of substitution of at least about 0.015 and (ii) which has an average molecular weight of between about 100,000 and 2,000,000, and (b) a primary external plasticizer, wherein the weight ratio of plasticizer to starch material is at least about 0.5:1.

* * * * *

UNITED STATES PATENT AND TRADEMARK OFFICE
CERTIFICATE OF CORRECTION

PATENT NO. : 6,649,188 B2 Page 1 of 1
DATED : November 18, 2003
INVENTOR(S) : Gregory M. Gilleland et al.

It is certified that error appears in the above-identified patent and that said Letters Patent is hereby corrected as shown below:

<u>Column 18,</u>
Line 39, delete "t e" and insert therefor -- the --.

Signed and Sealed this

Twenty-seventh Day of April, 2004

JON W. DUDAS
*Acting Director of the United States Patent and Trademark Office*